United States Patent [19]

Mayes

[11] Patent Number: 5,460,165

[45] Date of Patent: Oct. 24, 1995

[54] PROTECTIVE SHEATH FOR A SPECULUM AND METHOD OF USE

[76] Inventor: Robyn J. Mayes, 4625 SE. 20th, Del City, Okla. 73115

[21] Appl. No.: 245,182

[22] Filed: May 17, 1994

[51] Int. Cl.⁶ .................................................. A61B 1/32
[52] U.S. Cl. ........................ 600/186; 600/220; 600/203
[58] Field of Search .................................. 128/3, 10, 11, 128/16, 17, 18, 4, 844; 206/363, 438

[56] References Cited

U.S. PATENT DOCUMENTS

| | | | |
|---|---|---|---|
| 3,841,317 | 10/1974 | Awais | 128/17 |
| 4,206,750 | 6/1980 | Kaivola . | |
| 4,597,382 | 7/1986 | Perez, Jr. | 128/17 |
| 4,615,334 | 10/1986 | Jaeger . | |
| 4,686,966 | 8/1987 | Tsai . | |
| 4,693,871 | 9/1987 | Geller . | |
| 4,723,912 | 2/1988 | Nieusma . | |
| 4,884,559 | 12/1989 | Collins . | |
| 4,886,049 | 12/1989 | Darras | 128/4 |
| 4,971,036 | 11/1990 | Collins . | |
| 5,007,409 | 4/1991 | Pope | 128/17 |
| 5,050,586 | 9/1991 | Bonnell . | |
| 5,063,908 | 11/1991 | Collins . | |
| 5,072,720 | 12/1991 | Francis et al. . | |
| 5,139,422 | 8/1992 | Straihammer et al. . | |
| 5,156,165 | 10/1992 | Wu | 128/844 |
| 5,228,851 | 7/1993 | Burton | 128/4 X |
| 5,243,966 | 9/1993 | Ng | 128/3 |
| 5,329,937 | 7/1994 | Krstevich et al. | 128/17 |

Primary Examiner—Richard J. Apley
Assistant Examiner—Beverly M. Flanagan
Attorney, Agent, or Firm—Dunlap & Codding

[57] ABSTRACT

A disposable protective sheath for covering the dilating members of a speculum which are partially insertable into the vaginal cavity of a patient during a gynecological endoscopic examination. The sheath protects against transmission of potentially harmful micro-organisms via the speculum while still allowing visual and instrumental access to the vaginal cavity by the examining physician, yet the sheath does not interfere with the normal operation of the speculum.

19 Claims, 4 Drawing Sheets

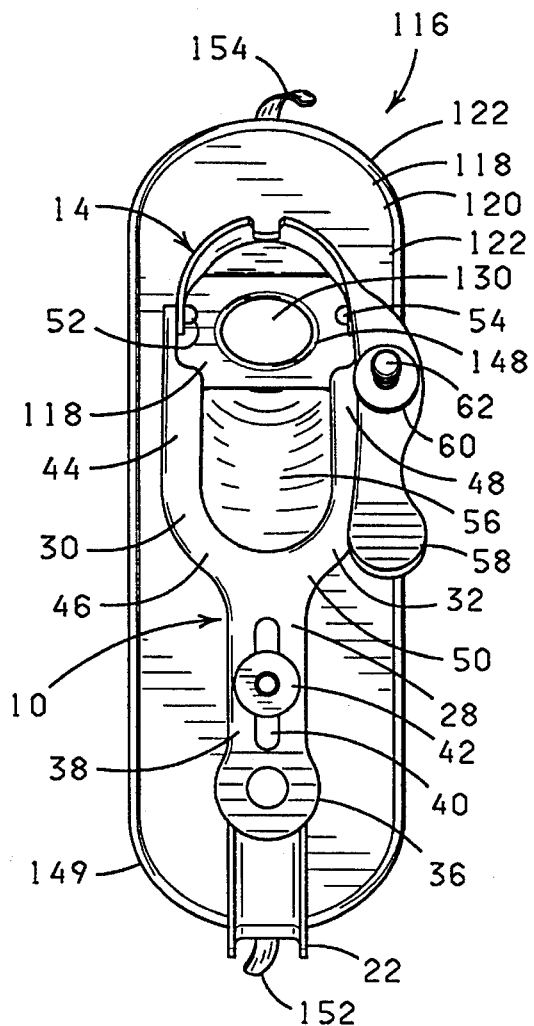
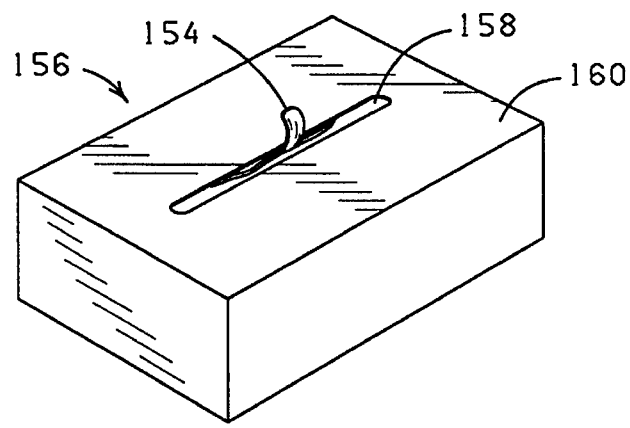
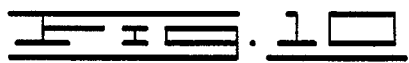

PROTECTIVE SHEATH FOR A SPECULUM AND METHOD OF USE

FIELD OF THE INVENTION

The present invention relates to protective sheaths for medical instruments and methods of using same. More particularly, the present invention relates to protective sheaths for a speculum and methods of using same.

BACKGROUND OF THE INVENTION

Ineffective or improper sterilization of medical instruments used for gynecological examinations has long been a concern for the medical community as well as for women in general. Many cases have been documented wherein women have contracted serious illnesses from contaminated gynecological instruments, some of which can lead to sterility or stillbirth. This concern has intensified since the identification of the human immunodeficiency virus (HIV), the cause of acquired immune deficiency syndrome (AIDS) in humans, which usually leads to death.

While most hospitals and clinics are equipped to autoclave (heat sterilize) medical instruments, some facilities still use alcohol to sterilize instruments. While autoclaving is a more effective method of sterilization, some germs can resist even this level of sterilization. Furthermore, improper sterilization can occur in either method, in which case a patient may be exposed to a greater spectrum of harmful strains of virus or bacteria.

A common medical instrument used in gynecological examinations is a speculum which typically comprises one or two duck-billed dilating members which are inserted into the vaginal cavity to afford the examining physician greater visual and instrumental access to the vaginal cavity. While disposable specula are known in the art, these have proven in practice to be cost inefficient. Therefore, most gynecological examinations are carried out using a metal speculum which must be sterilized after each use. This sterilization of the speculum necessarily induces the previously mentioned concerns.

BRIEF DESCRIPTION OF THE DRAWINGS

FIG. 9 is a plan view of the protective sheath and speculum of FIG. 7 showing the speculum in an examination position wherein the ends of the dilating members are spatially separated.

FIG. 10 is a container for storing a plurality of the protective sheaths of FIG. 2, FIG. 4. or FIG. 7.

DESCRIPTION OF THE PREFERRED EMBODIMENTS

Figure 1:
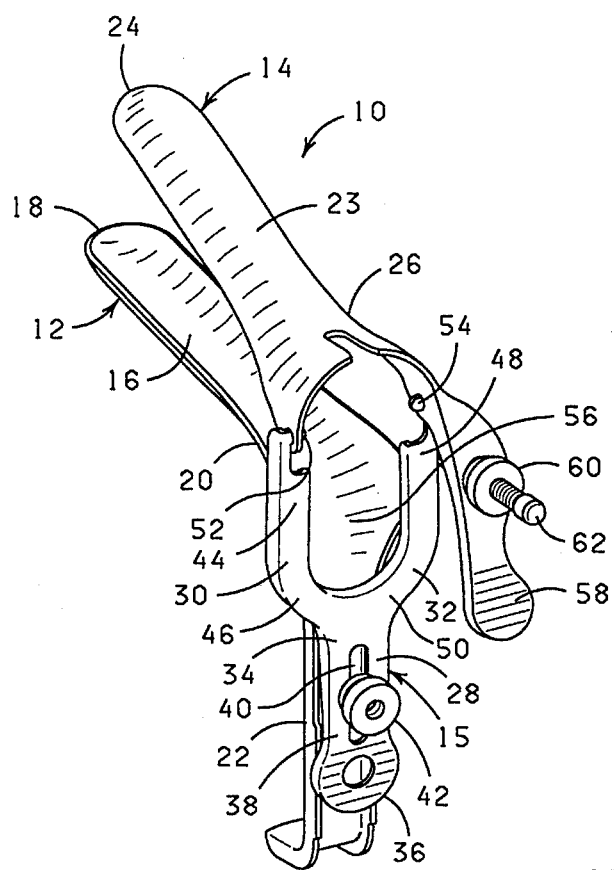
FIG. 1 is a perspective view of a typical prior art speculum used in gynecological examinations.

Shown in FIG. 1 is a prior art speculum of the type used in gynecological examinations, generally indicated by the reference numeral 10. The speculum 10 comprises a first dilating member 12, a second dilating member 14 and a connector assembly 15 for connecting the first and second dilating members 12 and 14 such that the second dilating member 14 can be selectively moved relative to the first dilating member 12. The first dilating member 12 comprises a body portion 16 having a first end 18 and a second end 20, and a handle portion 22 integrally connected to the second end 20 of the body portion 16. The second dilating member 14 comprises a body portion 23 having a first end 24 and a second end 26. The first ends 18 and 24 of the dilating members 12 and 14 are substantially duck-bill shaped to enhance insertion of the dilating members 12 and 14 into the vaginal cavity of a patient.

The connector assembly 15 is adjustably mounted to the handle portion 22 of the first dilating member 12. The connector assembly is substantially y-shaped and has a leg member 28, a first arm member 30 and a second arm member 32. The leg member 28 has a first end 34, a second end 36 and a body section 38. The body section 38 has a slot 40 formed therethrough. A first securing screw (not shown) fixed to the handle portion 22 of the first dilating member 12 projects through the slot 40 thereby allowing the connecting assembly 15 to be adjusted in relation to the first dilating member 12 to the limits defined by the slot 40. A first securing nut 42 may be threadably secured to the first securing screw (not shown) to frictionally secure the connecting assembly 15 relative to the first dilating member 12.

The first arm member 30 has a first end 44 and a second end 46. Likewise, the second arm member 32 has a first end 48 and a second end 50. The second ends 46 and 50 of the first and second arm members 30 and 32 are integrally connected to the first end 34 of the leg member 28 and initially extend generally laterally from the leg member 28 and thereafter curving to a position wherein the first and second arm members 30 and 32 extend substantially parallel to the leg member 28.

A first pin 52 extends inwardly from the first end 44 of the first arm member 30 and a second pin 54 extends inwardly from the first end 48 of the second arm member 32. The second end 26 of the second dilating member 14 is pivotally connect to the first and second pins 52 and 54 whereby an examination aperture 56 is formed between the arm members 30 and 32 of the connecting assembly 15, the second end 20 of the body portion 16 of the first dilating member 12, and the second end 26 of the body portion 23 of the second dilating member 14. The examination aperture 56 may be enlarged or reduced by adjusting the connecting assembly 15 relative to the handle portion 22 of the first dilating member 12.

A thumb press 58 connected to the second end 26 of the second dilating member 14 is utilized to selectively move the dilating members 12 and 14 between an insertion position (not shown) and an examination position.

In the insertion position, the first end 18 of the body portion 16 of the first dilating member 12 and the first end 24 of the body portion 23 of the second dilating member 14 are substantially adjacently disposed. In this position, the dilating members 12 and 14 may be partially inserted into the vaginal cavity of the patient. The thumb press 58 is then pressed to move the second dilating member 14 relative to the first dilating member 12 so that the first and second dilating members are disposed in an examination position wherein the first end 18 of the body portion 16 of the first dilating member 12 and the first end 24 of the body portion 23 of the second dilating member 14 are spatially separated, as shown in FIG. 1. A second securing nut 60 may then be threadably secured to a second securing screw 62 which is connected to the connecting assembly 15 and extends through an aperture (not shown) formed in the thumb press 58 to retain the first and second dilating members 12 and 14 in the examination position. The examining physician may then examine the patient by looking through the examination aperture 56 defined by the connecting assembly 15 into the vaginal cavity.

Figure 2:
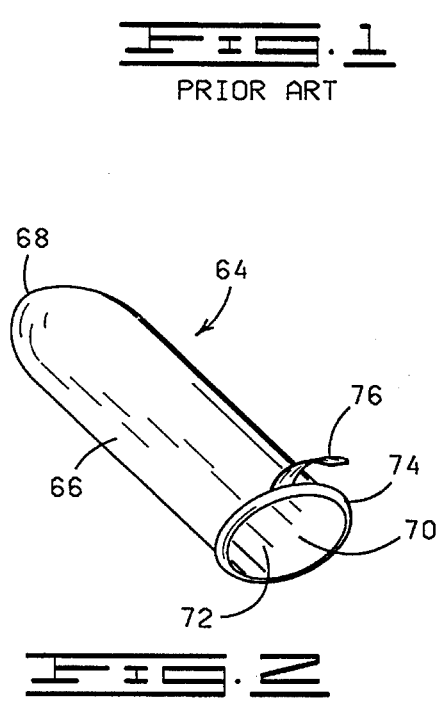
FIG. 2 is a perspective view of a protective sheath for a speculum constructed in accordance with the present invention.

Shown in FIG. 2 is a protective sheath 64 constructed in accordance with the present invention for isolating the first and second dilating members 12 and 14 from contact with the patient during an examination. One of the sheaths 64 is positioned about a portion of the body portion 16 of the first dilating member 12 and another of the sheaths 64 is positioned about the body portion 23 of the second dilating member 14 so that the patient is protected from transmission of potentially harmful micro-organisms that may be present on the speculum 10 without impeding the examining physician's view through the examination aperture 56 of the speculum 10.

The sheath 64 comprises a body portion 66 having a closed end 68, an open end 70 and a dilating member receiving passageway 72 formed therebetween. The sheath 64 further comprises a reinforcing member 74 formed about the open end 70 of the body portion 66 for preventing the body portion 66 of the sheath 64 from tearing when the sheath 64 is being positioned about the first and second dilating members 12 and 14 of the speculum 10. Additionally, a tab 76 is connected to the sheath 64 substantially adjacent to the open end 70 of the body portion 66 so as to extend outwardly therefrom substantially as shown to facilitate the positioning of the sheath 64 about the first and second dilating members 12 and 14 of the speculum 10. Preferably, the tab 76, which enhances the positioning of the sheaths 64 on the first and second dilating members 12 and 14 of the speculum 10 as well as the removal of the sheaths 64 from the first and second dilating members 12 and 14 of the speculum 10, is connected to the reinforcing member 74 so as to allow the tab 76 to be pulled with greater force without tearing the body portion 66 of the sheath 64.

The sheath 64 can have any suitable shape provided that it substantially conforms to at least a portion of the dilating members 12 and 14. To properly isolate the first and second dilating members 12 and 14 of the speculum 10 from the patient when the protective sheath 64 is positioned about the first and second dilating members 12 and 14, the sheath 64 is constructed from a material which is substantially impervious to fluids, particularly body fluids which can transmit harmful micro-organisms. The material forming the sheath 64 is also desirably fabricated of an elastomeric material so that one of the sheaths 64 may be stretched about each of the dilating members 12 and 14. The material will also have sufficient memory so that one of the sheaths 64 would substantially envelop one of the dilating members 12 or 14 when the material returns to its non-stretched state. A sheath 64 constructed of a natural or man-made polymer exhibits the previously mentioned characteristics. An example, but not by way of limitation, of such a material is rubber or, more particularly, latex.

The sheath 64 is positioned about the first dilating member 12 by partially inserting the first end 18 of the body portion 16 of the first dilating member 12 into the dilating member receiving passageway 72 of the body portion 66 of the sheath 64 via the open end 70 of the body portion 66. The reinforcing member 74 formed about the open end 70 of the body portion 66 of the sheath 64 facilitates the insertion of the first end 18 of the body portion 16 of the first dilating member 12 into the open end 70 of the body portion 66 of the sheath 64 by imparting at least some rigidity to the open end 70 of the body portion 66 whereby the open end 70 of the body portion 66 is at least partially retained in an open condition. The reinforcing member 74 also functions to prevent the body portion 66 of the sheath 64 from tearing when the sheath 64 is positioned about the first dilating member 12.

After the first end 18 of the body portion 16 of the first dilating member 12 has been partially inserted into the dilating member receiving passageway 72 of the body portion 66 of the sheath 64, the body portion 66 of the sheath 64 is positioned about the first dilating member 12 by pulling the reinforcing member 74 or the tab 76 whereby the sheath 64 is pulled over the first dilating member 12 thereby forcing the first dilating member 12 through the dilating member receiving passageway 72 until the sheath 64 substantially surrounds and encompasses the first dilating member 12 and the closed end 68 of the body portion 66 of the sheath 64 is disposed substantially adjacent to the first end 18 of the body portion 16 of the first dilating member 12.

Figure 3:
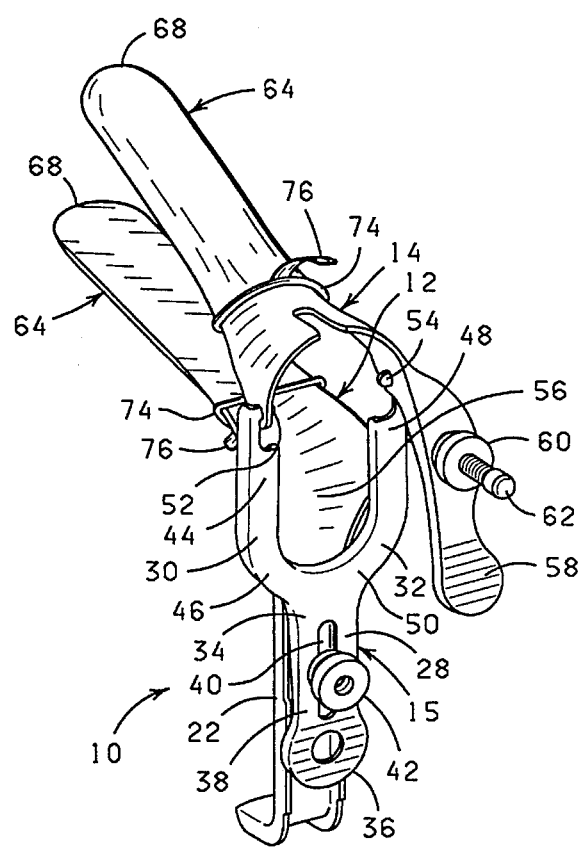
FIG. 3 is a perspective view of two protective sheaths of FIG. 2 positioned about the dilating members of the speculum of FIG. 1.

After the sheath 64 has been positioned about the first dilating member 12, another of the sheaths 64 is similarly positioned about the second dilating member 14. The first and second dilating members 12 and 14 of the speculum 10 are thereby covered (FIG. 3) to protect the patient from any potentially harmful micro-organisms that may be present on the first and second dilating members 12 and 14 of the speculum 10.

Although the speculum 10 shown includes the first and second dilating members 12 and 14, it should be noted that some specula (not shown) are constructed to have only the one dilating member which is similar in construction to the first dilating member 12 of the speculum 10. When a speculum (not shown) having only one dilating member is utilized, only one sheath 64 will be needed to cover the dilating member of the speculum to properly protect the patient. In such instances, the sheath 64 is positioned about the dilating member in substantially the same manner as hereinbefore described with reference to the first dilating member 12 of the speculum 10.

Figure 4:
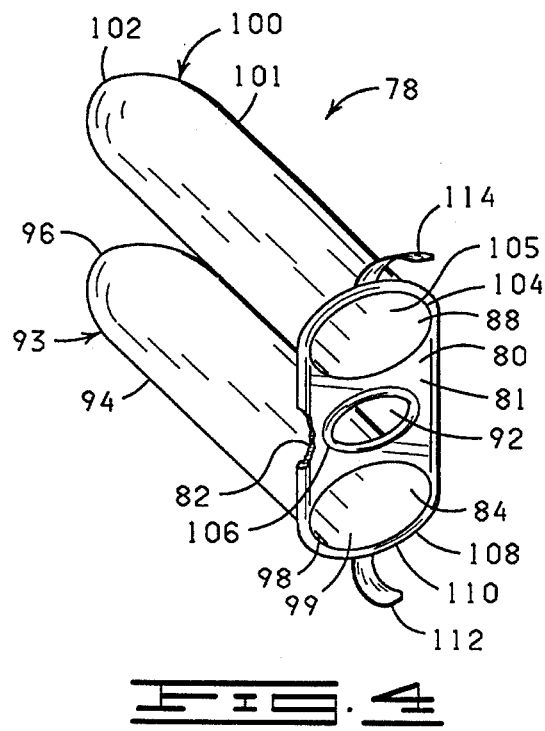
FIG. 4 is a perspective view of a second embodiment of a protective sheath for a speculum constructed in accordance with the present invention.

Shown in FIG. 4 is a second embodiment of a protective sheath assembly constructed in accordance with the present invention and generally designated by the reference numeral 78. The sheath assembly 78 comprises an apron 80 having a first side 81, a second side 82, a first aperture 84 formed therethrough and adapted to receive the first dilating member 12 of the speculum 10, a second aperture 88 formed therethrough and adapted to receive the second dilating member 14 of the speculum 10, and a medial aperture 92 formed therethrough for reasons which will be described in more detail hereinafter. The apertures 84, 88 and 92 are in a substantially linear arrangement with the medial aperture 92 being located between the first and second apertures 84 and 88.

A first sheath member 93 extends from the second side 82 of the apron 80 and the first sheath member 93 is provided with a body portion 94 having a closed end 96, an open end 98 and a first dilating member receiving passageway 99 formed therebetween. The open end 98 of the body portion 94 of the first sheath member 93 is aligned with the first aperture 84 in the apron 80. Similarly, a second sheath member 100 extends from the second side 82 of the apron 80 and the second sheath member 100 is provided with a body portion 101 having a closed end 102, an open end 104 and a second dilating member receiving passageway 105 formed therebetween. The open end 104 of the body portion 101 of the second sheath member 100 is aligned with the second aperture 88 in the apron 80. Desirably, the apron 80 and the first and second sheath members 93 and 100 are of seamless unitary construction to ensure that the sheath assembly 78 is impervious to body fluids and potentially harmful micro-organisms.

A reinforcing member 106 is disposed about the medial aperture 92 of the apron 80. The reinforcing member 106 prevents the apron 80 from tearing when the medial aperture 92 in the apron 80 is stretched during an examination.

A reinforcing member 108 is desirably disposed about an outer periphery 110 of the apron 80. The reinforcing member 108 prevents the apron 80 from tearing when the first and second body portions 94 and 101 of the first and second sheath members 93 and 100 are disposed over the first and second dilating members 12 and 14 of the speculum 10. A first tab 112 and a second tab 114 are connected to the apron 80, the first and second tabs 112 and 114 being substantially adjacently disposed to the outer periphery 110 of the apron 80. Preferably, the tabs 112 and 114, which enhance positioning the first and second sheath members 93 and 100 on the first and second dilating members 12 and 14 of the speculum 10 as well as removal of the first and second sheath members 93 and 100 from the first and second dilating members 12 and 14 of the speculum 10, are connected to the reinforcing member 108 so as to allow the tabs 112 and 114 to be pulled with greater force without tearing the apron 80 of the sheath assembly 78.

The body portions 94 and 101 of the first and second sheath members 93 and 100 may have any suitable shape provided that they substantially conform to at least a portion of the first and second dilating members 12 and 14. To properly isolate the speculum 10 from the patient when the first and second sheath members 93 and 100 of the protective sheath assembly 78 are positioned about the first and second dilating members 12 and 14, the sheath assembly 78 is constructed from a material which is substantially impervious to fluids, particularly body fluids which can transmit harmful microorganisms. The material forming the sheath assembly 78 is also desirably fabricated of an elastomeric material so that the sheath assembly 78 may be stretched about the first and second dilating members 12 and 14 of the speculum 10. The material also desirably possesses sufficient memory so that the first and second sheath members 93 and 100 substantially envelop the first and second dilating members 12 and 14 when the material returns to its non-stretched state. A material suitable for the fabrication of the sheath assembly 78 is a natural or man-made polymer which exhibits the previously mentioned characteristics. An example, but not by way of limitation, of such a material is rubber or, more particularly, latex.

The sheath assembly 78 is positioned about the speculum 10 by placing the first end 18 of the body portion 16 of the first dilating member 12 substantially adjacent to the first aperture 84 in the apron 80, and placing the first end 24 of the body portion 23 of the second dilating member 14 substantially adjacent to the second aperture 88 in the apron 80. The first end 18 of the body portion 16 of the first dilating member 12 is thereafter partially inserted through the first aperture 84 of the apron 80 and into the first dilating member receiving passageway 99 of the body portion 94 of the first sheath member 93. About simultaneously, the first end 24 of the body portion 23 of the second dilating member 14 is partially inserted through the second aperture 88 of the apron 80 and into the second dilating member receiving passageway 105 of the body portion 101 of the second sheath member 100.

The body portion 94 and the body portion 101 of the first and second sheath members 93 and 100 are then positioned about the first and second dilating members 12 and 14 of the speculum 10 by pulling the first tab 112 and the second tab 114 to simultaneously pull the body portions 94 and 101 of the first and second sheath members 93 and 100 over the first and second dilating members 12 and 14. The first tab 112 and the second tab 114 are pulled to move the body portions 94 and 101 of the first and second sheath members 93 and 100 over the first and second dilating members 12 and 14 until the body portion 94 of the first sheath member 93 substantially surrounds and encompasses the first dilating member 12 and the closed end 96 of the body portion 94 of the first sheath member 93 is disposed substantially adjacent to the first end 18 of the body portion 16 of the first dilating member 12, and the body portion 101 of the second sheath member 100 substantially surrounds and encompasses the second dilating member 14 and the closed end 102 of the second body portion 101 of the second sheath member 100 is disposed substantially adjacent to the first end 24 of the body portion 23 of the second dilating member 14 (FIG. 6).

Figure 6:
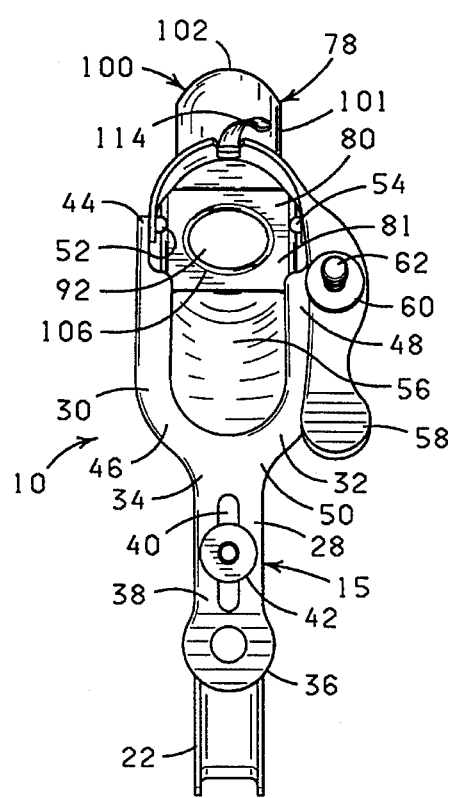
FIG. 6 is a plan view of the protective sheath and speculum of FIG. 4 showing the speculum in an examination position wherein the ends of the dilating members are spatially separated.

At this point, the medial aperture 92 formed in the apron 80 is necessarily disposed between the second end 20 of the body portion 16 of the first dilating member 12 and the second end 26 of the body portion 23 of the second dilating member 14 whereby the medial aperture 92 is aligned with the examination aperture 56 of the speculum 10 (FIG. 6).

After the sheath assembly 78 is positioned about the speculum 10 as previously described, the speculum 10 may be inserted into the vaginal cavity of the patient. Thereafter, the examining physician has visual and instrumental access through the examination aperture 56 of the speculum 10 and the medial aperture 92 in the apron 80 of the sheath assembly 78 into the vaginal cavity. When positioned on the speculum 10 in this manner, the sheath assembly 78 does not interfere with the normal operation of the speculum 10. The reinforcing member 106 disposed about the medial aperture 92 of the apron 80 allows the medial aperture 92 to be stretched without tearing the apron 80 so as to not inhibit access through the examination aperture 56 of the speculum 10. The elastomeric qualities of the sheath assembly 78 allow the medial aperture 92 to return to its original shape after the instruments have been removed.

Figure 7:
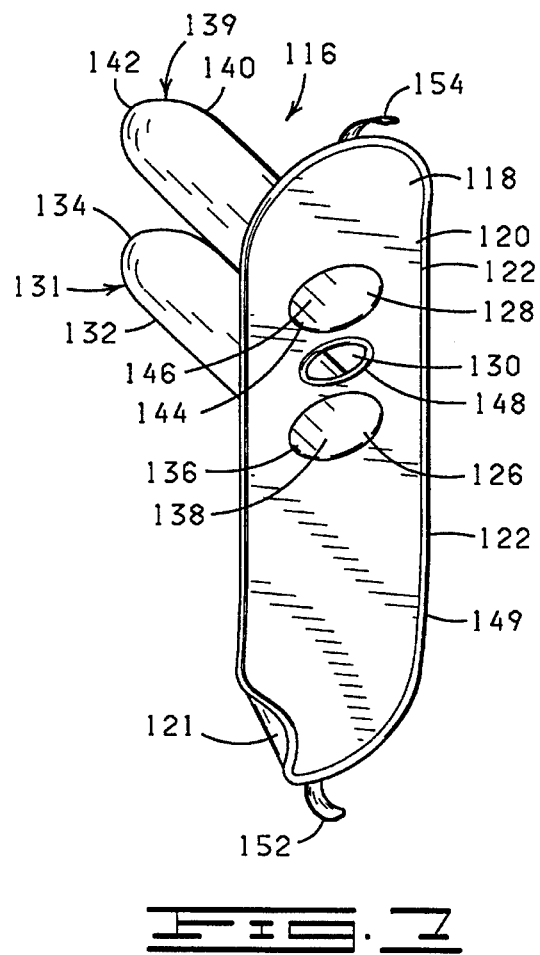
FIG. 7 is a perspective view of a third embodiment of a protective sheath for a speculum constructed in accordance with the present invention.

Shown in FIG. 7 is a third embodiment of a protective sheath assembly constructed in accordance with the present invention and generally designated by the reference numeral 116. The sheath assembly 116 is similar to the sheath assembly 78 of FIGS. 4–6 except that the sheath assembly 116 of FIG. 7 comprises an extended apron 118 to more completely isolate the patient from the speculum 10 as well as to provide more privacy to the patient during the examination. The apron 118 of the sheath assembly 116 has a first side 120, a second side 121, an outer periphery 122, a first aperture 126 formed therethrough and adapted to receive the first dilating member 12 of the speculum 10, a second aperture 128 formed therethrough and adapted to receive the second dilating member 14 of the speculum 10, and a medial aperture 130 formed therethrough for reasons which will be described in more detail hereinafter. The apertures 126, 128 and 130 are in a substantially linear arrangement with the medial aperture 130 being located between the first and second apertures 126 and 128.

A first sheath member 131 extends from the second side 121 of the apron 118 and the first sheath member 131 is provided with a body portion 132 having a closed end 134, an open end 136 and a first dilating member receiving passageway 138 formed therebetween. The open end 136 of the body portion 132 of the first sheath member 131 is aligned with the first aperture 126 in the apron 118. Similarly, a second sheath member 139 extends from the second side 120 of the apron 118 and the second sheath member 139 is provided with a body portion 140 having a closed end 142, an open end 144 and a second dilating member receiving passageway 146 formed therebetween. The open end 144 of the body portion 140 of the second sheath member 139 is aligned with the second aperture 128 in the apron 118. Desirably, the apron 118 and the first and second sheath members 131 and 139 are of seamless unitary construction to ensure that the sheath assembly 116 is impervious to body fluids and potentially harmful microorganisms.

A reinforcing member 148 is disposed about the medial aperture 130 of the apron 118. The reinforcing member 148 prevents the apron 118 from tearing when the medial aperture 130 in the apron 118 is stretched during an examination.

A reinforcing member 149 is desirably disposed about the outer periphery 122 of the apron 118. The reinforcing member 149 prevents the apron 118 from tearing when the first and second body portions 132 and 140 of the first and second sheath members 131 and 139 are disposed in a covering position over the first and second dilating members 12 and 14 of the speculum 10. A first tab 152 and a second tab 154 are connected to the apron 118, the tabs 152 and 154 being substantially adjacently disposed to the outer periphery 122 of the apron 118. Preferably, the tabs 152 and 154, which enhance positioning the first and second sheath members 131 and 139 on the first and second dilating members 12 and 14 of the speculum 10 as well as removal of the first and second sheath members 131 and 139 from the first and second dilating members 12 and 14 of the speculum 10, are connected to the reinforcing member 149 so as to allow the tabs 152 and 154 to be pulled with greater force without tearing the apron 118 of the sheath assembly 116.

The body portions 132 and 140 of the first and second sheath members 131 and 139 may have any suitable shape provided that they substantially conform to at least a portion of the first and second dilating members 12 and 14. To properly isolate the speculum 10 from the patient when the first and second sheath members 131 and 139 of the protective sheath assembly 116 is positioned about the first and second dilating members 12 and 14, the sheath assembly 116 is constructed from a material which is substantially impervious to fluids, particularly body fluids which can transmit harmful micro-organisms. The material forming the sheath assembly 116 is desirably fabricated of an elastomeric material in order to provide the first and second sheath members 131 and 139 of the sheath assembly 116 with the desired capability of substantially conforming to the shape of the first and second dilating members 12 and 14 of the speculum 10. A material suitable for the fabrication of the sheath assembly 116 is a natural or man-made polymer which exhibits the previously mentioned characteristics. An example, but not by way of limitation, of such a material is rubber or, more particularly, latex.

Figure 5:
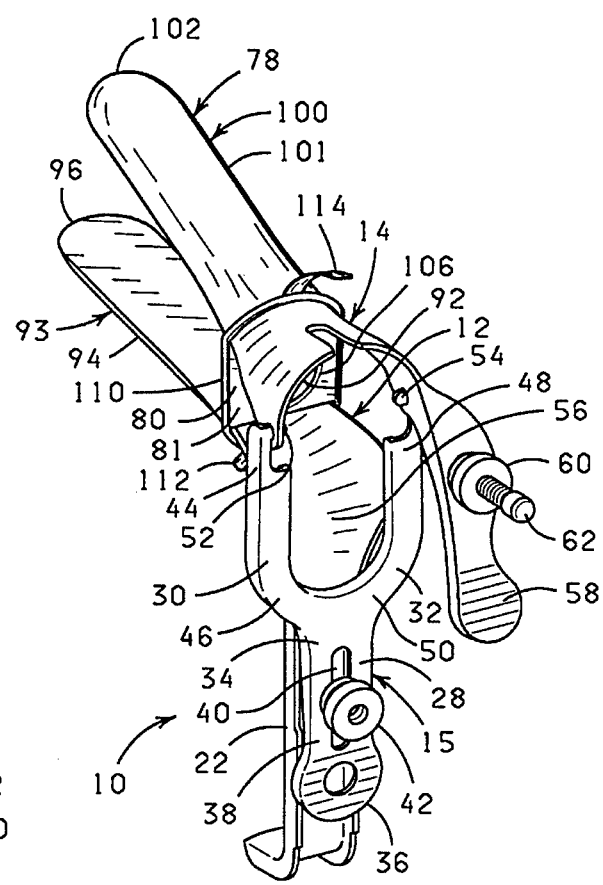
FIG. 5 is a perspective view of the protective sheath of FIG. 4 positioned about the dilating members of the speculum of FIG. 1.
Figure 8:
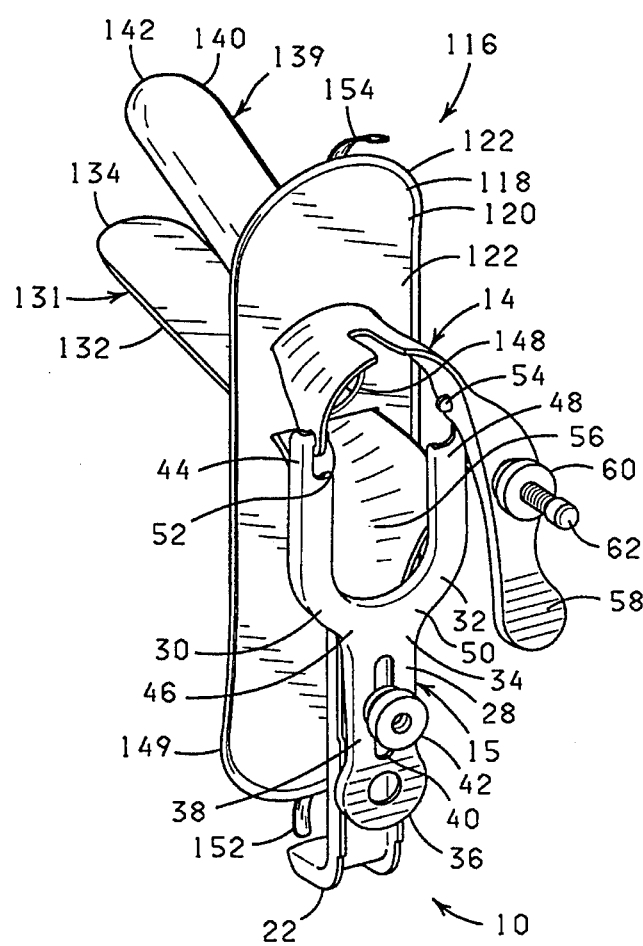
FIG. 8 is a perspective view of the protective sheath of FIG. 7 positioned about the dilating members of the speculum of FIG. 1.

The sheath assembly 116 is positioned about the speculum 10 in exactly the same manner as previously described for positioning the sheath assembly 78 of FIGS. 4–6 about the speculum 10. The sheath assembly 116 is disposed about the speculum 10 in a position substantially as shown in FIGS. 8 and 9.

After the first and second sheath members 131 and 139 of the sheath assembly 116 are positioned about the first and second dilating members 12 and 14 of the speculum 10 as previously described, the first and second dilating members 12 and 14 of the speculum 10 may be inserted into the vaginal cavity of the patient. Thereafter, the examining physician has visual and instrumental access through the examination aperture 56 of the speculum 10 and the medial aperture 130 in the sheath assembly 116 into the vaginal cavity. The reinforcing member 148 disposed about the medial aperture 130 formed in the apron 118 allows the medial aperture 130 to be stretched without tearing the apron 118 so as to not inhibit access through the examination aperture 56 of the speculum 10. The elastomeric qualities of the sheath assembly 116 allow the medial aperture 130 to return to its original shape after the instruments have been removed.

As shown in FIG. 10, one or more of the sheath assemblies 116 may be provided in a container 156. When provided in a container 156, the sheath assembly 116 is positioned so that the first tab 152 of the sheath assembly 116 is accessible to the user through an opening 158 formed in an upper side 160 of the container 156. The opening 158 is desirably formed by removing a strip portion (not shown) from the container 156. The sheath assembly 116 may then be removed from the container 156 by pulling the first tab 152 of the sheath assembly 116. When the container 156 contains a plurality of the sheath assemblies 116, the sheath assemblies 116 are desirably positioned in such a manner in the container 156 so that, when the uppermost disposed sheath assembly 116 is removed from the container 156, the first tab 152 of the next sheath assembly 116 in the container 156 extends outwardly from the container 156 via the opening 158.

Although a container 156 containing a plurality of the sheath assemblies 116 constructed for use with a speculum 10 having two dilating members 12 and 14 is shown, it should be understood that the container 156 may contain any of the types of protective sheath assemblies described previously.

If the sheath assemblies 116 contained in the container 156 are provided with the second tab 154, then the first tab 152 of the uppermost disposed sheath assembly 116 may be pulled to remove at least a portion of the uppermost disposed sheath assembly 116. The second tab 154 of the uppermost sheath assembly 116 desirably remains frictionally secured within the container 156 while the first and second dilating members 12 and 14 of the speculum 10 are at least partially inserted into the first and second sheath members 131 and 139 of the sheath assembly 116. The speculum 10 and sheath assembly 116 may then be pulled to remove the remainder of the uppermost disposed sheath assembly 116 from the container 156. Such dispensing containers 156 are well known in the medical field. For example, surgical gloves have been provided in such containers for many years.

Changes may be made in the embodiments of the invention described herein, or in parts or elements of the embodiments described herein, or in the steps or sequence of steps of the methods described herein, without departing from the spirit and/or scope of the invention as defined in the following claims.

What is claimed is:

1. A disposable protective sheath for a speculum wherein the speculum comprises a first dilating member and a second dilating member partially insertable into the vaginal cavity of a patient, wherein the first dilating member has a handle portion and a body portion with a first and second end, the handle portion being adjustably connected to a connecting assembly which, in cooperation with the first and second dilating members, define an examination aperture for the speculum, and wherein the second dilating member has a first end and a second end, the second end of the second dilating member being connected to the connecting assembly such that the second dilating member of the speculum is selectively moveable between an insertion position wherein the first ends of the first and second dilating members are substantially adjacently disposed, and an examination position wherein the first ends of the first and second dilating members are spatially separated, the protective sheath comprising:

an apron having a first side, a second side and an outer periphery; the apron further having a first aperture adapted to receive the first dilating member of the speculum, a second aperture adapted to receive the second dilating member of the speculum, and a medial aperture alignable with the examination aperture of the speculum so as to provide a substantially unrestricted view through the examination aperture of the speculum;

a first sheath member extending from the second side of the apron, the first sheath member comprising a body portion having a closed end, an open end and a first dilating member receiving passageway extending therebetween, the open end of the body portion of the first sheath member being aligned with the first aperture in the apron so that the first end of the body portion of the first dilating member of the speculum is insertable into the first dilating member receiving passageway of the body portion of the first sheath member via the first aperture so that the first sheath member is disposed over the first dilating member of the speculum and the closed end of the body portion of the first sheath member is disposed substantially adjacent the first end of the first dilating member and the first sheath member substantially conforms to the shape of the first dilating member of the speculum and substantially encloses the portion of the first dilating member of the speculum insertable into the vaginal cavity; and a second sheath member extending from the second side of the apron, the second sheath member comprising a body portion having a closed end, an open end and a second dilating member receiving passageway extending therebetween, the open end of the body portion of the second sheath member being aligned with the second aperture in the apron so that the first end of the second dilating member of the speculum is insertable into the second dilating member receiving passageway of the body portion of the second sheath member via the second aperture so that the second sheath member is disposed over the second dilating member of the speculum and the closed end of the body portion of the second sheath member is disposed substantially adjacent the first end of the second dilating member of the speculum and the second sheath member substantially conforms to the shape of the second dilating member of the speculum and substantially encloses the portion of the second dilating member of the speculum insertable into the vaginal cavity.

2. The protective sheath of claim 1 further comprising at least one tab means connected to the apron for enhancing the positioning of the first and second sheath members about the first and second dilating members of the speculum and for enhancing removal of the sheath from the speculum.

3. The protective sheath of claim 1 further comprising reinforcing means disposed about the outer periphery of the apron for preventing tearing of the apron during positioning of the first and second sheath members about the first and second dilating members of the speculum.

4. The protective sheath of claim 3 further comprising at least one tab means connected to the reinforcing means disposed about the outer periphery of the apron for enhancing positioning of the first and second sheath members about the first and second dilating members of the speculum and for enhancing removal of the first and second sheath members of the sheath from the first and second dilating member of the speculum.

5. The protective sheath of claim 1 wherein the sheath is constructed from an elastomeric material substantially impervious to body fluids and wherein the elastomeric material possesses sufficient elasticity to permit the first and second sheath members to be stretched about the first and second dilating members of the speculum and to allow the medial aperture of the apron to be stretched when the first and second dilating members of the speculum are moved to the examination position.

6. The protective sheath of claim 1 further comprising a reinforcing member disposed about the medial aperture in the apron for preventing the apron from tearing when the medial aperture is stretched.

7. A speculum and disposable protective sheath assembly for use in gynecological examinations comprising:

a speculum comprising:
a first dilating member having a handle portion and a body portion, the body portion of the first dilating member having a first end and a second end,
a second dilating member having a first end and a second end; and
connecting means for connecting the second end of the second dilating member to the handle portion of the first dilating member such that the second dilating member is selectively moveable between an insertion position wherein the first ends of the first and second dilating members are substantially adjacently disposed and an examination position wherein the first ends of the first and second dilating members are spatially separated, the connecting means, in cooperation with the first and second dilating members, define an examination aperture; and a disposable protective sheath constructed from an elastomeric material substantially impervious to body fluids wherein the sheath comprises:
an apron having a first side, a second side and an outer periphery, the apron further having a first aperture adapted to receive the first dilating member of the speculum, a second aperture adapted to receive the second dilating member of the speculum and a medial aperture alignable with the examination aperture of the speculum;

a first sheath member extending from the second side of the apron, the first sheath member comprising a body portion having a closed end, an open end and a first dilating member receiving passageway extending therebetween, the open end of the body portion of the first sheath member being aligned with the first aperture in the apron so that the first end of the body portion of the first dilating member of the speculum is insertable into the first dilating member receiving passageway of the body portion of the first sheath member via the first aperture so that the first sheath member is disposed over the first dilating member of the speculum and the closed end of the body portion of the first sheath member is disposed substantially adjacent the first end of the body portion of the first dilating member of the speculum and the first sheath member substantially conforms to the shape of the first dilating member of the speculum and substantially encloses the portion of the first dilating member of the speculum insertable into the vaginal cavity; and a second sheath member extending from the second side of the apron, the second sheath member comprising a body portion having a closed end, an open end and a second dilating member receiving passageway extending therebetween, the open end of the body portion of the second sheath member being aligned with the second aperture in the apron so that the first end of the second dilating member of the speculum is insertable into the second dilating member receiving passageway of the body portion of the second sheath member via the second aperture so that the second sheath member is disposed over the second dilating member of the speculum and the closed end of the body portion of the second sheath member is disposed substantially adjacent the first end of the second dilating member of the speculum and the second sheath member substantially conforms to the shape of the second dilating member of the speculum and substantially encloses the portion of the second dilating member of the speculum insertable into the vaginal cavity.

8. The speculum and disposable protective sheath assembly of claim 7 wherein the sheath further comprises at least one tab means connected to the outer periphery of the apron for enhancing the positioning of the first and second sheath members about the first and second dilating members of the speculum and for removing the sheath from the speculum.

9. The speculum and disposable protective sheath assembly of claim 7 wherein the sheath further comprises a reinforcing means disposed about the periphery of the apron for preventing tearing of the apron during positioning of the first and second sheath members about the first and second dilating members of the speculum.

10. The speculum and disposable protective sheath assembly of claim 9 wherein the sheath further comprises at least one tab means connected to the reinforcing means for enhancing positioning of the first and second sheath members of the sheath about the first and second dilating members of the speculum and for enhancing removal of the first and second sheath members of the sheath from the first and second dilating members of the speculum.

11. The speculum and disposable protective sheath assembly of claim 7 wherein the sheath further comprises reinforcing means disposed about the medial aperture in the apron of the sheath for preventing the apron from tearing when the medial aperture is stretched.

12. A method for providing a disposable protective sheath about a speculum having at least one dilating member wherein the dilating member is provided with a body portion insertable into the vagina of a patient, the body portion of the dilating member having a first end and a second end, the method comprising the steps of:

providing a protective sheath comprising a body portion having a closed end, an open end and a dilating member receiving passageway extending therebetween, the protective sheath having at least one tab extending from the body portion of the protective sheath near the open end thereof;

providing a container containing at least one protective sheath wherein the tab of the protective sheath extends outwardly from the container;

pulling the tab on the body portion of the protective sheath to remove the protective sheath from the container; and inserting the first end of the dilating member of the speculum into the dilating member receiving passageway of the body portion of the protective sheath via the open end thereof and thereafter pulling the protective sheath over the dilating member of the speculum so that the closed end of the body portion of the protective sheath is disposed substantially adjacent the first end of the dilating member of the speculum and the body portion of the protective sheath substantially encloses the portion of the dilating member of the speculum insertable into the vaginal cavity and substantially conforms to the shape of the dilating member of the speculum and thereby prevents transmission of microorganisms present on the dilating member of the speculum to the patient during a gynecological examination.

13. A method for providing a disposable protective sheath for a speculum wherein the speculum comprises a first dilating member and a second dilating member; the first dilating member having a handle portion and a body portion, the body portion of the first dilating member having a first end and a second end, the second dilating member having a first end and a second end, wherein the handle portion of the first dilating member is connected to the second end of the second dilating member by a connecting assembly such that an examination aperture is defined by the connecting assembly in cooperation with the first and second dilating members, and the second dilating member is selectively moveable relative to the first dilating member between an insertion position wherein the first ends of the first and second dilating members are substantially adjacently disposed and an examination position wherein the first ends of the first and second dilating members are spatially separated, the method comprising the steps of:

providing a protective sheath comprising:

an apron having a first side, a second side, an outer periphery, a first aperture adapted to receive the first dilating member of the speculum, a second aperture adapted to receive the second dilating member of the speculum, and a medial aperture alignable with the examination aperture of the speculum, a first sheath member extending from the second side of the apron, the first sheath member comprising a body portion having a closed end, an open end and a dilating member receiving passageway extending therebetween, the open end of the body portion of the first sheath member being aligned with the first aperture in the apron; and a second sheath member extending from the second side of the apron, the second sheath member comprising a body portion having a closed end, an open end and a dilating member receiving passageway extending therebetween, the open end of the body portion of the second sheath member being aligned with the second aperture in the apron; and inserting the first end of the body portion of the first dilating member of the speculum into the first dilating member receiving passageway of the first sheath member via the first aperture of the apron;

inserting the first end of the second dilating member of the speculum into the second dilating member receiving passageway of the second sheath member via the second aperture of the apron; and pulling the first and second sheath members over the first and second dilating members of the speculum so that the closed end of the first sheath member is disposed substantially adjacent the first end of the body portion of the first dilating member of the speculum and the closed end of the second sheath member is disposed substantially adjacent the first end of the second dilating member of the speculum whereby the first and second sheath members substantially enclose portions of the first and second dilating members insertable into the vaginal cavity and substantially conform to the shape of the first and second dilating members of the speculum, and the medial aperture of the apron is disposed between the second end of the body portion of the first dilating member and the second end of the body portion of the second dilating member and is aligned with the examination aperture of the speculum to provide an unobstructed view through the examination aperture and the medial aperture into the vaginal cavity when the speculum is configured in an examination position.

14. The method of claim 13 wherein, in the step of providing a protective sheath, the protective sheath further comprises a first tab and a second tab, the first and second tabs being connected to the outer periphery of the apron; and wherein the method further comprises the steps of:

providing a container containing at least one protective sheath wherein the first tab of the protective sheath extends outwardly from the container;

pulling the first tab of the protective sheath to remove at least a portion of the protective sheath from the container to expose the first and second apertures of the apron; and wherein the step of positioning the first and second sheath members of the protective sheath about the first and second dilating members of the speculum further comprises:

inserting the first end of the body portion of the first dilating member of the speculum into the first dilating member receiving passageway of the first sheath member via the first aperture of the apron;

inserting the first end of the body portion of the second dilating member of the speculum into the second dilating member receiving passageway of the second sheath member via the second aperture of the apron; and removing the remainder of the protective sheath from the container and positioning the first and second dilating members of the speculum in the first and second sheath members such that the first ends of the first and second dilating members of the speculum are disposed substantially against the closed ends of the body portions of the first and second sheath members.

15. A method for providing a disposable protective sheath about a speculum, the method comprising the steps of:

providing a speculum comprising at least one dilating member with a first end and a second end;

providing a protective sheath comprising a body portion having a closed end, an open end and a dilating member receiving passageway extending therebetween, the protective sheath further comprising at least one tab extending from the body portion of the protective sheath near the open end thereof;

providing a container having an opening formed therein, the container containing at least one protective sheath;

pulling the tab of the protective sheath so as to remove the protective sheath from the container; and positioning the protective sheath about the dilating member of the speculum by disposing the dilating member of the speculum in the dilating member receiving passageway of the body portion of the protective sheath such that the body portion of the protective sheath substantially surrounds and encompasses the dilating member of the speculum and thereby prevents transmission of potentially harmful micro-organisms present on the speculum to the patient during a gynecological examination.

16. A method for providing a disposable protective sheath about a speculum comprising the steps of:

providing a speculum comprising:

a first dilating member having a handle portion and a body portion, the body portion having a first end and a second end, a second dilating member having a first end and a second end; and connecting means for connecting the second end of the second dilating member to the handle portion of the first dilating member such that the second dilating member is selectively moveable between an insertion position wherein the first ends of the first and second dilating members are substantially adjacently disposed and an examination position wherein the first ends of the first and second dilating members are spatially separated, the connecting means defining an examination aperture; and providing a protective sheath constructed of an elastomeric material substantially impervious to body fluids wherein the sheath comprises:

an apron having a first side, a second side and an outer periphery, the apron further having a first aperture adapted to receive the first dilating member of the speculum, a second aperture adapted to receive the second dilating member of the speculum and a medial aperture alignable with the examination aperture defined by the connecting means;

a first sheath member extending from the second side of the apron, the first sheath member comprising a body portion having a closed end, an open end and a first dilating member receiving passageway extending therebetween, the open end of the body portion of the first sheath member being aligned with the first aperture in the apron; and a second sheath member extending from the second side of the apron, the second sheath member comprising a body portion having a closed end, an open end and a second dilating member receiving passageway extending therebetween, the open end of the body portion of the second sheath member being aligned with the second aperture in the apron;

positioning the protective sheath about the first and second dilating members of the speculum by inserting the first end of the body portion of the first dilating member of the speculum into the first dilating member receiving passageway of the protective sheath via the first aperture in the apron and inserting the first end of the second dilating member of the speculum into the second dilating member receiving passageway of the protective sheath via the second aperture in the apron and thereafter pulling the first and second sheath members over the first and second dilating members of the speculum to a position wherein the closed end of the first sheath member is disposed substantially adjacent the first end of the body portion of the first dilating member of the speculum and the closed end of the second sheath member is disposed substantially adjacent the first end of the second dilating member of the speculum and the first and second sheath members of the protective sheath substantially enclose the portion of the first and second dilating members of the speculum insertable into the vaginal cavity and substantially conform to the shape of the first and second dilating members of the speculum and whereby the medial aperture of the apron is disposed between the second ends of the first and second dilating members of the speculum and substantially aligned with the examination aperture of the speculum to provide an unobstructed view through the examination aperture and the medial aperture of the apron into the vaginal cavity when the speculum is configured in the examination position.

17. The method of claim 16 wherein, in the step of providing a protective sheath, the apron of the protective sheath is characterized as having an outer periphery and wherein the protective sheath further comprises a first tab and a second tab, the first and second tabs being connected to the outer periphery of the apron, and wherein the method further comprises the steps of:

providing a container containing at least one protective sheath, the container having an opening therein through which the protective sheath can be removed;

pulling the first tab of the protective sheath to remove at least a portion of the protective sheath from the container and thereby expose the first and second apertures in the apron while maintaining the second tab of the protective sheath frictionally secured within the container; and wherein the step of positioning the sheath about the dilating members of the speculum further comprises:
at least partially inserting the first end of the body portion of the first dilating member of the speculum into the first dilating member receiving passageway of the first sheath member via the first aperture in the apron;
at least partially inserting the first end of the second dilating member of the speculum into the second dilating member receiving passageway of the second sheath member via the second aperture of the apron; and
removing the remainder of the protective sheath from the container and positioning the first and second dilating members of the speculum in the first and second sheaths such that the first ends of the first and second dilating members of the speculum are disposed substantially against the closed ends of the body portions of the first and second sheath members.

18. A method for conducting a gynecological examination comprising the steps of:

providing a speculum comprising:
a first dilating member having a handle portion and a body portion, the body portion having a first end and a second end,
a second dilating member having a first end and a second end; and
connecting means for connecting the second end of the second dilating member to the handle portion of the first dilating member such that the second dilating member is selectively moveable between an insertion position wherein the first ends of the first and second dilating members are substantially adjacently disposed and an examination position wherein the first ends of the first and second dilating members are spatially separated, the connecting means defining an examination aperture; and providing a protective sheath constructed of an elastomeric material substantially impervious to body fluids wherein the sheath comprises:
an apron having a first side, a second side and an outer periphery, the apron further having a first aperture adapted to receive the first dilating member of the speculum, a second aperture adapted to receive the second dilating member of the speculum and a medial aperture alignable with the examination aperture defined by the connecting means;
a first sheath member extending from the second side of the apron, the first sheath member comprising a body portion having a closed end, an open end and a first dilating member receiving passageway extending therebetween, the open end of the body portion of the first sheath member being aligned with the first aperture in the apron; and
a second sheath member extending from the second side of the apron, the second sheath member comprising a body portion having a closed end, an open end and a second dilating member receiving passageway extending therebetween, the open end of the body portion of the second sheath member being aligned with the second aperture in the apron;

positioning the protective sheath about the first and second dilating members of the speculum by inserting the first end of the body portion of the first dilating member of the speculum into the first dilating member receiving passageway of the protective sheath via the first aperture in the apron and inserting the first end of the second dilating member of the speculum into the second dilating member receiving passageway of the protective sheath via the second aperture in the apron and thereafter pulling the first and second sheath members over the first and second dilating members of the speculum to a position wherein the closed end of the first sheath member is disposed substantially adjacent the first end of the body portion of the first dilating member of the speculum and the closed end of the second sheath member is disposed substantially adjacent the first end of the second dilating member of the speculum and the first and second sheath members of the protective sheath substantially enclose the portion of the first and second dilating members of the speculum insertable into the vaginal cavity and substantially conform to the shape of the first and second dilating members of the speculum and whereby the medial aperture of the apron is disposed between the second ends of the first and second dilating members of the speculum and substantially aligned with the examination aperture of the speculum to provide an unobstructed view through the examination aperture and the medial aperture of the apron into the vaginal cavity when the speculum is configured in the examination position;

positioning the first and second dilating members of the speculum in an insertion position;

at least partially inserting the first dilating member of the speculum having the first sheath member of the protective sheath disposed thereon and the second dilating member of the speculum having the second sheath member of the protective sheath disposed thereon into the vaginal cavity; and positioning the first and second dilating members of the speculum in the examination position to allow an examining physician to have visual and instrumental access to the vaginal cavity;

restoring the first and second dilating members of the speculum substantially to the insertion position at the completion of the examination;

removing the first and second dilating members of the speculum from the vaginal cavity; and removing the first and second sheath members of the protective sheath from the first and second dilating members of the speculum.

19. Disposable protective sheaths positionable about dilating members of a speculum wherein the speculum comprises a first dilating member and a second dilating member, each of the first and second dilating members having a first end and a second end, the second ends of the first and second dilating members operably connected so as to permit the first and second dilating members to be selectively moved between an insertion position and an examination position, the first and second dilating members being partially insertable into a vaginal cavity of a patient and wherein each of the protective sheaths comprises:

a body portion having a closed end, an open end and a dilating member receiving passageway formed therebetween, the first dilating member of the speculum insertable into the dilating member receiving passageway of the body portion of one sheath via the open end thereof so that the closed end of the body portion of the sheath is disposed substantially adjacent the first end of the first dilating member of the speculum and the body portion of the sheath substantially conforms to the shape of the first dilating member of the speculum and encloses the portion of the first dilating member insertable into the vaginal cavity, the second dilating member of the speculum insertable into the dilating member receiving passageway of the body portion of another sheath via the open end thereof so that the closed end of the body portion of the sheath is disposed substantially adjacent the first end of the second dilating member of the speculum and the body portion of the sheath substantially conforms to the shape of the second dilating member of the speculum and encloses the portion of the second dilating member insertable into the vaginal cavity whereby the protective sheaths cooperate to prevent transmission of potentially harmful micro-organisms present on the first and second dilating members of the speculum to the patient during a gynecological examination; and an apron positionable on the patient so as to permit access to the vaginal cavity of the patient, the apron having at least one aperture for permitting the first and second dilating members of the speculum having the protective sheaths disposed thereon to be inserted through the aperture and within the vaginal cavity while permitting a substantially unrestricted view of the vaginal cavity.

* * * * *